(12) United States Patent
Stamm et al.

(10) Patent No.: US 12,426,843 B2
(45) Date of Patent: Sep. 30, 2025

(54) IMAGING SYSTEM WITH WIDE X-RAY BEAM AND CIRCUMFERENTIALLY ARRANGED DETECTION MECHANISM

(71) Applicant: Varex Imaging Corporation, Salt Lake City, UT (US)

(72) Inventors: Michael Stamm, Schaffhausen (CH); David T. Nisius, Des Plaines, IL (US); Daniel Shedlock, Knoxville, TN (US); Josh M. Star-Lack, Palo Alto, CA (US); Gregory C. Andrews, West Jordan, UT (US); Matthias Ehrat, Hettlingen (CH)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 266 days.

(21) Appl. No.: 17/821,637

(22) Filed: Aug. 23, 2022

(65) Prior Publication Data

US 2023/0056945 A1 Feb. 23, 2023

Related U.S. Application Data

(60) Provisional application No. 63/236,191, filed on Aug. 23, 2021.

(51) Int. Cl.
*A61B 6/00* (2024.01)
*A61B 6/03* (2006.01)
*G01V 5/222* (2024.01)

(52) U.S. Cl.
CPC .............. *A61B 6/482* (2013.01); *A61B 6/032* (2013.01); *G01V 5/222* (2024.01)

(58) Field of Classification Search
None
See application file for complete search history.

(56) References Cited

U.S. PATENT DOCUMENTS 5,091,862 A    2/1992  Hoffman et al.
5,740,224 A *  4/1998  Muller ................. G01N 23/044
                                                        378/11

(Continued)

FOREIGN PATENT DOCUMENTS

CN        112147165 A       12/2020

OTHER PUBLICATIONS

Han, Yueping, Han, Yan, Li, Ruihong, Wang, Liming; "Application of X-ray digital radiography to online automated inspection of interior assembly structures of complex products," Nuclear Instruments and Methods in Physics Research A A604 (2009) pp. 760-764.

*Primary Examiner* — Marcus H Taningco
(74) *Attorney, Agent, or Firm* — Dorsey & Whitney LLP

(57) ABSTRACT

An imaging system for inspecting multiple objects includes an x-ray source having a beam width greater than or equal to a threshold beam size. The multiple objects is irradiated by the x-ray source in respective controlled inspection positions. A detection mechanism is adapted to acquire respective images of the multiple objects in the respective controlled inspection positions. The detection mechanism includes one or more detectors arranged circumferentially around a central axis. At least one positioning mechanism is adapted to move the multiple objects into and out of the respective controlled inspection positions.

27 Claims, 6 Drawing Sheets

(56) References Cited

U.S. PATENT DOCUMENTS

| | | | | |
|---|---|---|---|---|
| 7,680,242 B2* | 3/2010 | Masuda | ................... | H01J 35/30 |
| | | | | 378/19 |
| 2004/0017888 A1* | 1/2004 | Seppi | ..................... | G01N 23/04 |
| | | | | 378/57 |
| 2006/0023835 A1* | 2/2006 | Seppi | ...................... | G01V 5/20 |
| | | | | 378/57 |
| 2008/0226023 A1* | 9/2008 | Masuda | ................. | G01N 23/04 |
| | | | | 378/19 |
| 2009/0110147 A1* | 4/2009 | Safai | ...................... | G21K 1/04 |
| | | | | 378/127 |
| 2010/0172561 A1* | 7/2010 | Ota | ....................... | G06T 11/006 |
| | | | | 378/19 |
| 2010/0329532 A1* | 12/2010 | Masuda | .............. | G01N 23/046 |
| | | | | 378/58 |
| 2011/0222648 A1* | 9/2011 | Tischenko | ............. | A61B 6/032 |
| | | | | 378/4 |
| 2013/0235971 A1* | 9/2013 | Oreper | ................. | G01T 1/2985 |
| | | | | 378/57 |
| 2014/0270054 A1* | 9/2014 | Sampayan | ........... | G01N 23/046 |
| | | | | 378/9 |
| 2020/0378907 A1* | 12/2020 | Morton | ................. | G01V 5/226 |

* cited by examiner

IMAGING SYSTEM WITH WIDE X-RAY BEAM AND CIRCUMFERENTIALLY ARRANGED DETECTION MECHANISM

CROSS-REFERENCE TO RELATED APPLICATIONS

This application claims priority to, and benefit of, U.S. Provisional Patent Application Ser. No. 63/236,191 filed on Aug. 23, 2021, which is hereby incorporated by reference in its entirety.

BACKGROUND

Imaging systems employ various types of radiation to generate images of objects. The images are used for a variety of purposes, such as for example, imaging for medical diagnosis and treatment, materials analysis and non-destructive testing, inspection of items and security applications. One example of the type of radiation employed is x-rays. A conventional x-ray tube creates a stream of energized electrons via a cathode. X-rays are generated when the electrons travel at a high speed and collide with a target surface on an anode. The x-rays interact with the object being imaged, and may be at least partially absorbed by the object, scattered or transmitted. A sensor can be employed to detect the signal intensity of the x-rays which have passed through the object unimpeded and/or scattered into the field of view of the sensor.

BRIEF DESCRIPTION OF THE DRAWINGS

The drawings described herein are for illustrative purposes only, are schematic in nature and are intended to be exemplary rather than to limit the scope of the disclosure.

Figure 1:
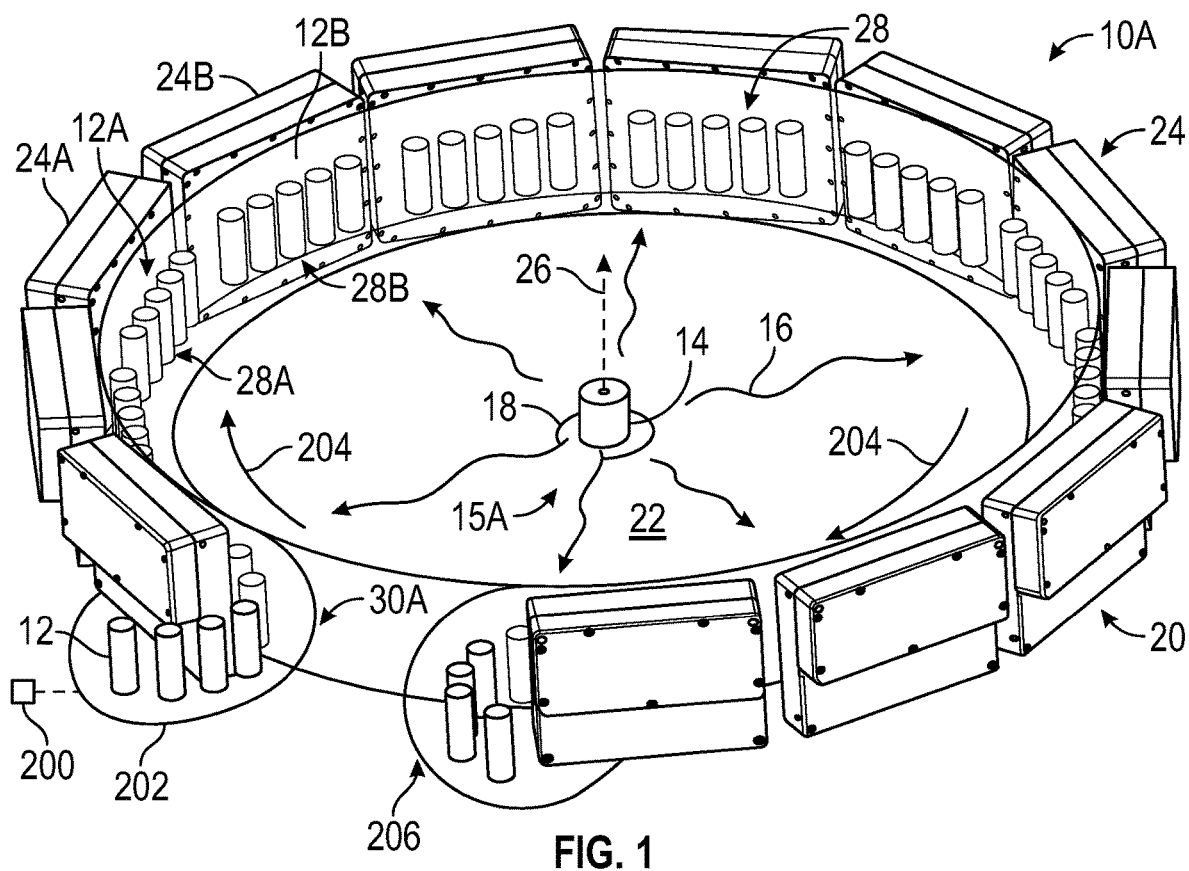
FIG. 1 is a schematic fragmentary perspective view of an imaging system having an x-ray source, in accordance with one embodiment of the present disclosure.

Representative embodiments of this disclosure are shown by way of non-limiting example in the drawings and are described in additional detail below. It should be understood, however, that the novel aspects of this disclosure are not limited to the particular forms illustrated in the above-enumerated drawings. Rather, the disclosure is to cover modifications, equivalents, combinations, sub-combinations, permutations, groupings, and alternatives falling within the scope of this disclosure as encompassed, for instance, by the appended claims.

DETAILED DESCRIPTION

Embodiments of the present disclosure are described herein. The disclosed embodiments are provided as examples and illustration of the various solutions. The drawings are not necessarily to scale, with some features possibly exaggerated or minimized to show particular details of interest. Therefore, specific structural and functional details disclosed herein are not to be interpreted as limiting, but merely as a representative basis for teaching one skilled in the art to variously employ disclosed structure and methodologies. Furthermore, the embodiments shown in the drawings, or the characteristics of various embodiments mentioned in the present description, are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

The embodiments described herein relate generally to imaging systems employing x-ray sources. More specifically, the disclosure relates to an imaging system for inspecting multiple objects, the imaging system having a wide-angled x-ray source and a detection mechanism with one or more detectors. Referring to the drawings, wherein like reference numbers refer to like components, FIG. 1 schematically illustrates an imaging system 10A for inspecting multiple objects 12. The imaging system 10A includes an x-ray source 14 generating a beam 16. The beam 16 is a wide-angled or panoramic beam defining a beam width 18 that is greater than or equal to a threshold beam size.

Many x-ray sources and systems use only a small part of the solid angle of a beam generated by an x-ray source. This results in a small amount of the generated x-rays being captured by the sensor, thereby limiting efficiency. In contrast, the imaging system 10A uses a much larger part of the solid angle of the beam 16, in combination with one or more digital detectors. This allows a high amount of the generated radiation to be captured and used. Additionally, the imaging system 10A enables a large number of the multiple objects 12 to be imaged simultaneously with a single x-ray source, resulting in a significantly lower inspection cost per object.

In some embodiments, the multiple objects 12 are imaged in two dimensions (2D), for example, with a threshold beam size of about 110 degrees. In a non-limiting example, beam width 18 extends between about 110 degrees and 340 degrees. In other embodiments, the multiple objects 12 are imaged in three dimensions (3D), with a threshold beam size of about one steradian. For example, the threshold beam size can be between 0.9 steradian and 1.5 steradian.

Referring to FIG. 1, a detection mechanism 20 is arranged in a radial fashion around the x-ray source 14 with the beam 16 emanating from a large part of the available solid angle.

This forms an inspection region 22 around the x-ray source 14, between the x-ray source 14 and detection mechanism 20. The parts to be inspected, i.e., the multiple objects 12 can travel through the inspection region 22 while being scanned by the detection mechanism 20. The multiple objects 12 can be a single, continuous (e.g., long) part instead of discrete separate objects. The multiple objects 12 can include, but are not limited to, battery cells, metal castings, plastic moldings, electronic devices and other industrial and commercial goods.

Referring to FIG. 1, the detection mechanism 20 is comprised of one or more detectors 24 arranged circumferentially around a central axis 26. The detection mechanism 20 can include multiple detectors 24 (see FIG. 1), which may be arranged in an annular fashion around the x-ray source 14. Alternatively, the detection mechanism 20 can include a single continuous or large detector (see FIG. 2). The detectors 24 can be flat or curved.

The detection mechanism 20 may include a two-dimensional imaging array of sensors for detecting the signal intensity transmitted through the multiple objects 12, such as a flat panel detector (e.g., an area indirect conversion detector with scintillators). For example, the detection mechanism 20 may include, but is not limited to, an amorphous silicon (a-Si), indium gallium zinc oxide (IGZO), or complementary metal-oxide-semiconductor (CMOS) flat panel detector. The detection mechanism 20 can include at least one line-scan detector, also referred to as a linear detector array or line scanner. The line-scan detector has a small number of pixels along its width relative to the number of pixels along its length. To allow the multiple objects 12 to be inspected with a line-scan detector, either the line-scan detector or the multiple objects 12 are moved back and forth in a direction perpendicular to the central axis 26. In some embodiments, the detection mechanism 20 includes a direct conversion image detector configured to directly convert the radiation into a signal. The direct conversion image detector may include but is not limited to, cadmium telluride (CdTe), cadmium zinc telluride (CdZnTe or CZT) and selenium-based sensors. The detection mechanism 20 can incorporate a dual scanning system with both linear detector arrays and direct conversion detectors.

As described below, the multiple objects 12 are irradiated by the x-ray source 14 in respective controlled inspection positions 28. Referring to FIG. 1, at least one positioning mechanism 30A is adapted to move the multiple objects 12 into and out of the respective controlled inspection positions 28 adjacent to the detection mechanism 20. The multiple objects 12 may travel through partial, complete or multiple orbits around the x-ray source 14. For example, the multiple objects 12 can orbit around the x-ray source 14 in a circular or elliptical fashion.

Figure 2:
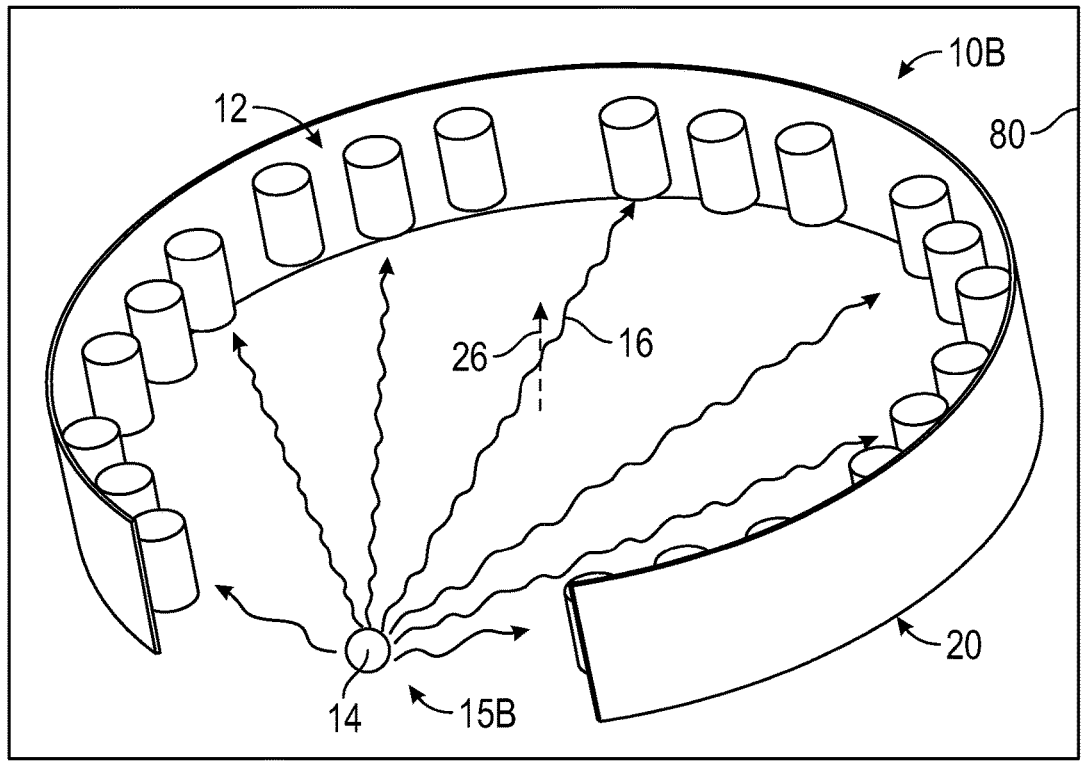
FIG. 2 is a schematic fragmentary perspective view of the imaging system in accordance with another embodiment of the present disclosure.

The positioning of the x-ray source 14 relative to the detection mechanism 20 may be varied. For example, the x-ray source 14 in the imaging system 10A shown in FIG. 1 is positioned at a central location 15A relative to the detection mechanism 20, along the central axis 26. An alternative embodiment is shown in FIG. 2. In the imaging system 10B shown in FIG. 2, the x-ray source 14 is placed in an off-center location 15B relative to the detection mechanism 20, such that the x-ray source 14 is shifted away from the central axis 26.

Figure 3:
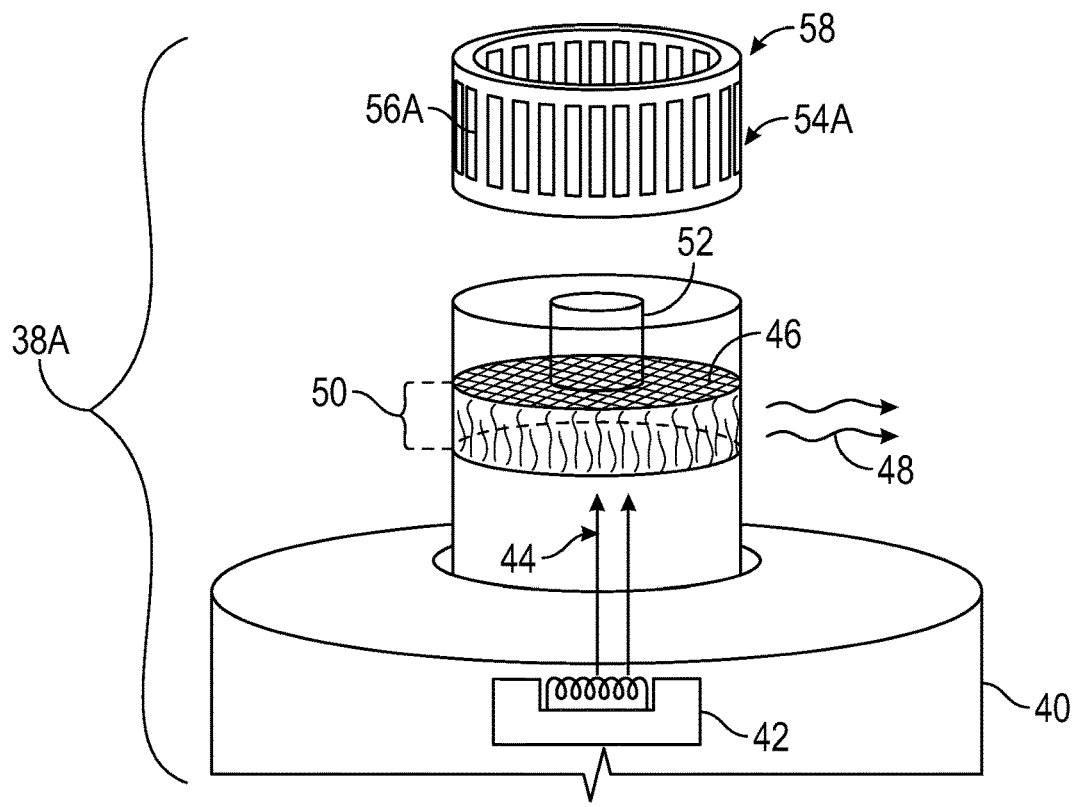
FIG. 3 is a schematic fragmentary exploded view of an exemplary x-ray source with an x-ray tube having a removable collimator.
Figure 4:
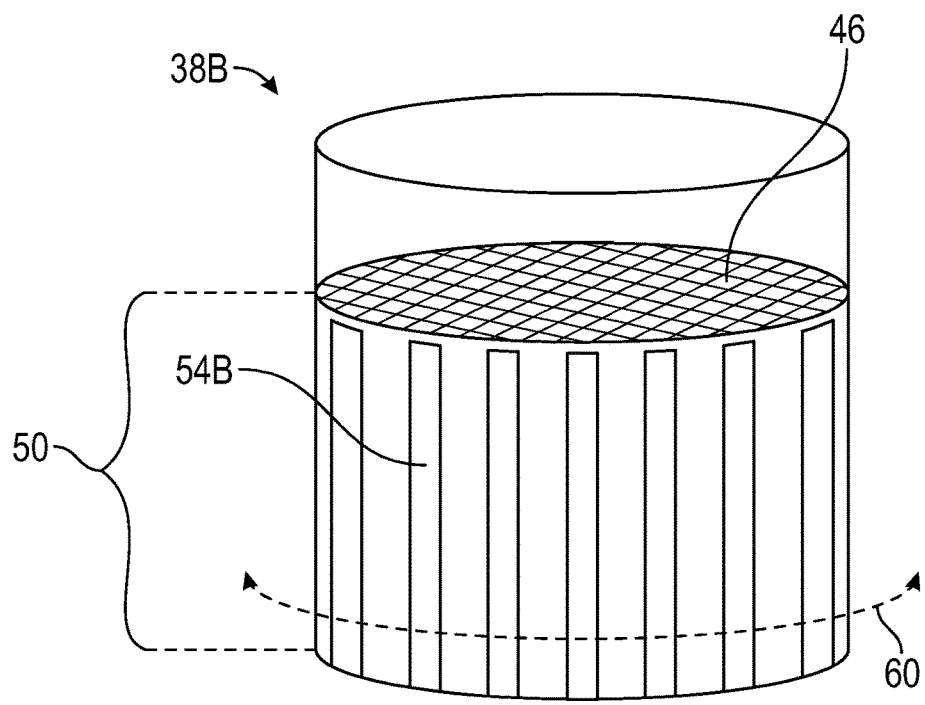
FIG. 4 is a schematic fragmentary perspective view of another exemplary x-ray source with an x-ray tube having an integrated collimator.

The x-ray source 14 includes at least one x-ray tube, the design of which may be varied based on the application at hand. FIG. 3 shows an exploded fragmentary view of an exemplary x-ray tube 38A that may be used in the x-ray source 14. The x-ray tube 38A includes a housing or tube can 40, which may be sealed to enclose a vacuum. Referring to FIG. 3, a cathode 42 is configured to generate an electron beam 44. The electron beam 44 is energized, directed towards and collides with an anode 46, resulting in the generation of x-rays 48. The cathode 42 includes an emitter, such as a coil emitter or flat emitter. Referring to FIG. 3, the x-rays 48 are emitted through an exit window 50. Referring to FIG. 4, the exit window 50 can extend circumferentially for about 360 degrees. The x-ray tube 38A includes an anode support structure 52, which may include a motor. For simplicity, structures for guiding the electron beam 44 are not shown. The anode 46 may be rotating or stationary. It is to be understood that the shape of the anode 46 may be varied based on the application at hand. For example, the anode 46 may be flat, cone shaped and/or arched. Anodes 46 that are cone or arch-shaped may allow for creation of specific spot shapes, while anodes 46 that are flat may allow for better interaction.

The imaging systems 10A, 10B of FIGS. 1-2 may incorporate a collimation mechanism to guide the beam 16. Examples of collimators 54A, 54B are shown in FIGS. 3-4. The collimators 54A, 54B include shielding to block radiation emitted in undesirable directions and a series of parallel openings (e.g., slits) to shape the emitted radiation. Referring to FIG. 3, the collimator 54A is removable and may be slipped-on or added to the x-ray tube 38A. The collimator 54A includes a plurality of apertures 56A constructed in an annular body 58, forming multiple effective focal spots. A focal spot is the area of the anode surface which receives the beam of electrons from the cathode.

Referring to FIG. 3, the collimator 54A is inserted and aligned relative to the exit window 50, such that it overlaps with the exit window 50. The collimator 54A may be installed interior of or exterior to the exit window 50. The slit size may be varied, depending on the energy of the x-rays employed, the size of the multiple objects 12 and other factors.

The collimator 54A of FIG. 3 provides a technical advantage that a single tube model (x-ray tube 38A) many be used with different collimators. For example, a collimator 54A with ten apertures can be employed with a set-up having ten detectors 24 (in the detection mechanism 20 of FIG. 1) and ten zones for the multiple objects 12 to be scanned. Likewise, a collimator 54A with twenty apertures may be employed with a set-up having twenty detectors 24 and twenty zones for the multiple objects 12 to be scanned.

Figure 5:
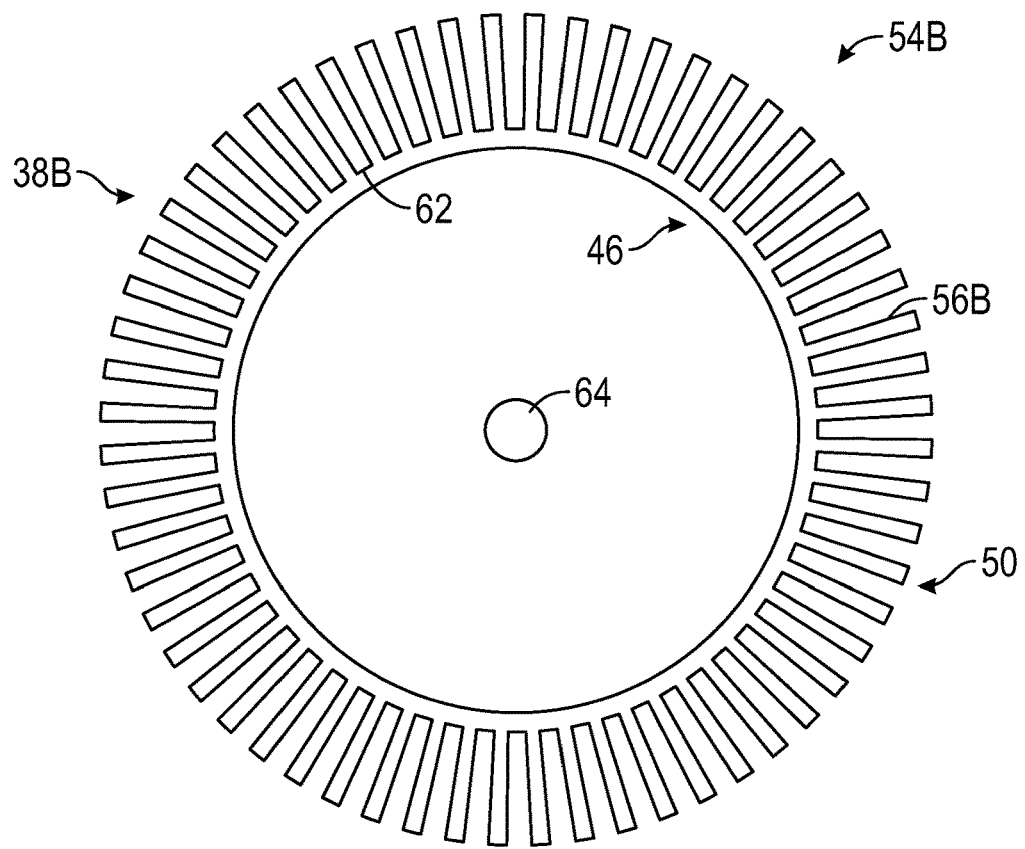
FIG. 5 is a schematic fragmentary sectional view through the x-ray source of FIG. 4.

FIG. 4 shows another exemplary collimator 54B that may be used with an x-ray tube 38B. FIG. 5 is a sectional view through axis 60 of FIG. 4. Referring to FIGS. 4-5, the collimator 54B includes a plurality of apertures 56B integrated into the structure of the x-ray tube 38B, forming multiple effective focal spots. This enables each scan volume to have a focal spot with an aspect ratio that is close to one-to-one. Referring to FIG. 5, the plurality of apertures 56B can be machined into the body of the anode 46, leaving an annular region 62 of supporting structure. In one example, the annular region 62 is about 0.5 mm, the inner wall of the anode 46 has a radius of about 10 mm, and the plurality of apertures 56B start and end at a radial distance of 10.5 mm and 15 mm, respectively. Referring to FIG. 4, the collimator 54B is aligned relative to the exit window 50, such that it overlaps it. The collimator 54B provides a technical advantage of being closer to the effective focal spot 64, resulting in less of the available beam being cut off by the collimator for a given geometry. The shape of the effective focal spot 64 is homogeneous along multiple axes.

Figure 6:
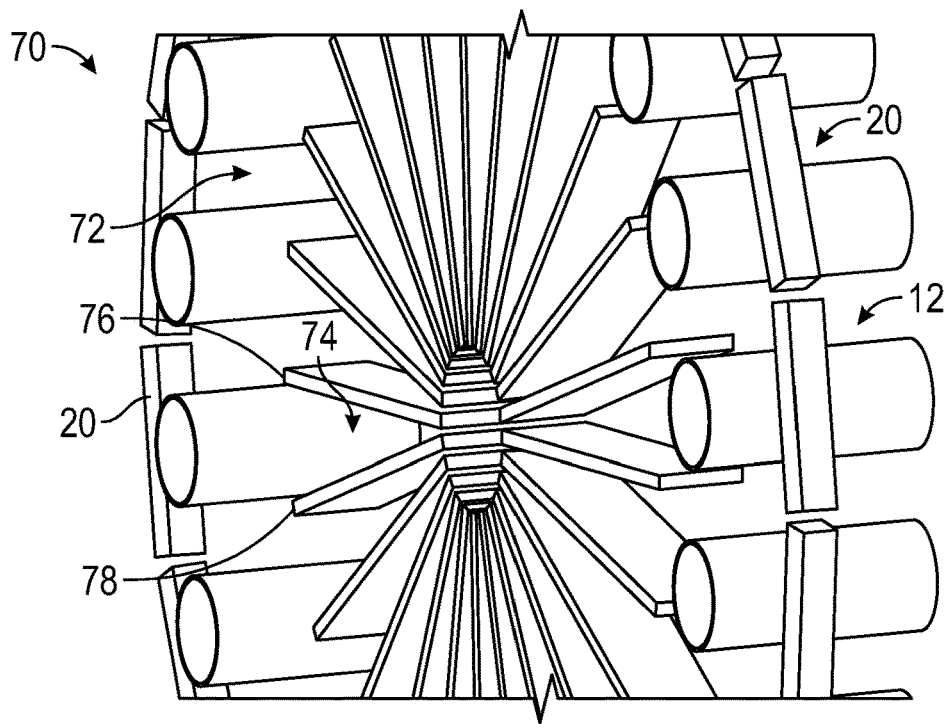
FIG. 6 is a schematic fragmentary perspective view of a scatter prevention mechanism employable in the imaging system.
Figure 7:
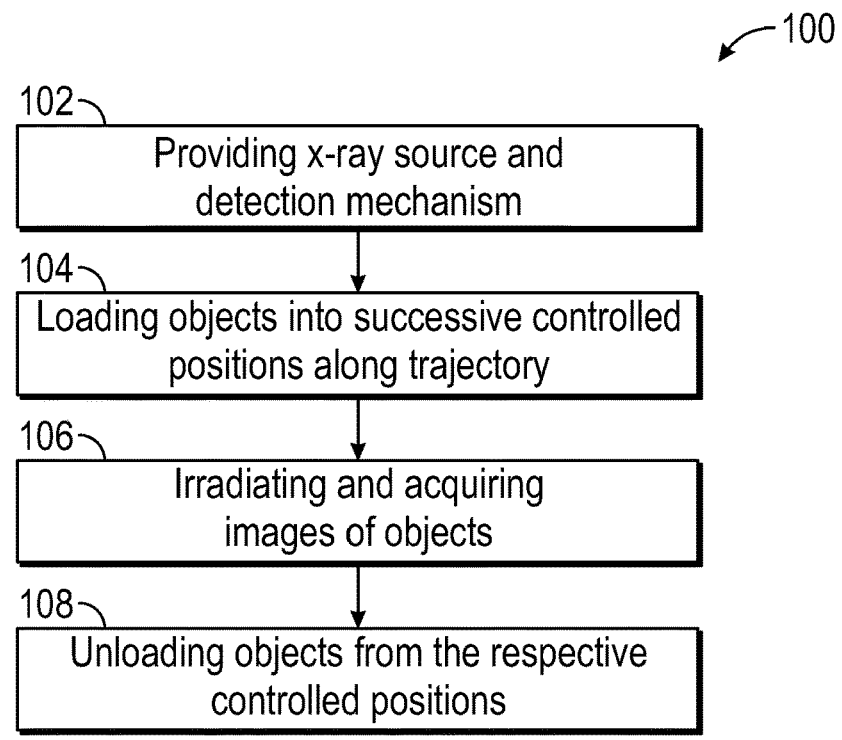
FIG. 7 is a flow chart describing an exemplary method for inspecting multiple objects with the imaging system.

The imaging systems 10A, 10B of FIGS. 1-2 can incorporate a scatter prevention mechanism 70, an example of which is shown in FIG. 6. Referring to FIG. 7, the scatter prevention mechanism 70 includes a plurality of vanes 72 radially distributed between the multiple objects 12. The plurality of vanes 72 divides the inspection region 22 into zone, such as inspection zone 74 between first vane 76 and second vane 78, surrounding each of the multiple objects 12 in order to minimize scattering. In each of the embodiments shown, a protective cabin 80 (shown in FIGS. 2 and 9) may be used to enclose the set-up, including the x-ray source 14 and detection mechanism 20. The protective cabin 80 can be sealed and maintained at a predetermined temperature and pressure. For example, the protective cabin 80 can be maintained at above ambient pressure to avoid contaminants in the inspection region 22. The protective cabin 80 can operate as a shielding mechanism by incorporating a shielding material, e.g., a lead lining.

Referring now to FIG. 7, a flowchart of a method 100 for inspecting the multiple objects 12 is shown. Method 100 need not be applied in the specific order recited herein. Furthermore, it is to be understood that some steps may be eliminated. Method 100 can be executed in real-time, continuously, systematically, sporadically and/or at regular timed intervals.

Method 100 can be embodied as computer-readable code or instructions stored on and partially executable by a controller 200 (see FIG. 1). The controller 200 has at least one processor and at least one memory (or non-transitory, tangible computer readable storage medium) on which instructions can be recorded for executing the method 100. The memory can store controller-executable instruction sets, and the processor can execute the controller-executable instruction sets stored in the memory M.

Per block 102 of FIG. 7, the method 100 includes providing an x-ray source 14 generating a beam 16. As described above, the beam 16 is a wide-angled or panoramic beam defining a beam width 18 that is greater than or equal to a threshold beam size. Also as described previously, the detection mechanism 20 is arranged circumferentially around the central axis 26, creating the inspection region 22 between the detection mechanism 20 and x-ray source 14.

Figure 8:
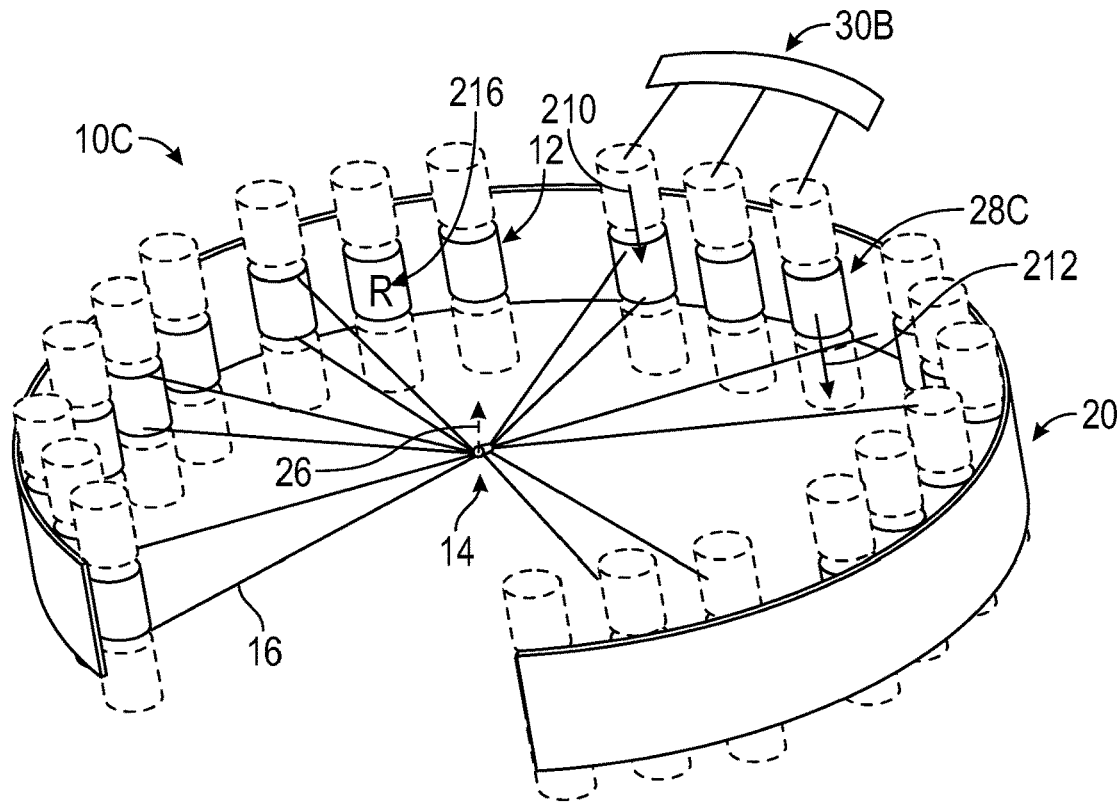
FIG. 8 is a schematic fragmentary perspective diagram illustrating an exemplary positioning mechanism useable in the imaging system.

Per block 104 of FIG. 7, the method 100 includes loading the multiple objects 12 into successive positions, referred to herein as respective controlled inspection positions 28, via at least one positioning mechanism, such as positioning mechanism 30A shown in FIG. 1 and positioning mechanism 30B shown in FIG. 8.

In the embodiment shown in FIG. 1, the positioning mechanism 30A is a conveyor belt configured to move the multiple objects 12 around the x-ray source 14. Here, the multiple objects 12 can enter and leave the inspection region 22 in approximately the same plane as the reference plane or radial surface formed by the beam 16. Referring to FIG. 1, the multiple objects 12 can be loaded at an entrance zone 202, travel through a trajectory 204 and be unloaded at the exit zone 206. As the multiple objects 12 travel through the inspection region 22 along the trajectory 204, the object can be sequentially scanned by two or more of the detectors 24. In other words, each of the multiple objects 12 can move between at least two of the detectors 24. For example, referring to FIG. 1, a first group 12A of the multiple objects 12 can be scanned by the detector 24A in the controlled inspection position 28A, simultaneously with a second group 12B of the multiple objects 12 being scanned by the detector 24B in the controlled inspection position 28B. The controlled inspection position refers to the location/position of the multiple objects 12 where the objects 12 are within scanning range of one or more of the detectors 24. The controlled inspection position may be defined relative to a three-dimensional coordinate system. In the next sequence, the first group 12A moves along the trajectory 204 and is scanned by the detector 24B. The movement of the multiple objects 12 can be controlled in a continuous or stepped manner. The controller 200 can be programmed with a specific trajectory 204 and time sequence for moving the multiple objects 12. The shape of the trajectory may be varied.

Referring now to the embodiment shown in FIG. 8, the positioning mechanism 30B loads the multiple objects 12 into the respective controlled inspection positions 28C in a loading direction 210 and unloads the multiple objects 12 in the unloading direction 212. In the imaging system 10C of FIG. 8, the multiple objects 12 enter into and leave the respective controlled inspection positions 28C in a direction parallel to the central axis 26, in a normal direction relative to the reference plane or radial surface of the beam 16. In some embodiments, the positioning mechanism 30B may include one or more vacuum gripper robots for automatically loading and unloading the multiple objects 12. The loading and/or unloading can be executed in one continuous motion or in a stepped motion. The movements of the multiple objects 12 may be into and out of the respective controlled inspection positions 28C may be synchronized and programmed into the controller 200.

In some embodiments, both the multiple objects 12 and the detection mechanism 20 are rotated around the central axis 26 at a predetermined or specified speed. It is to be understood that the loading and unloading mechanism for the multiple objects 12 may be varied based on the application at hand.

Figure 9:
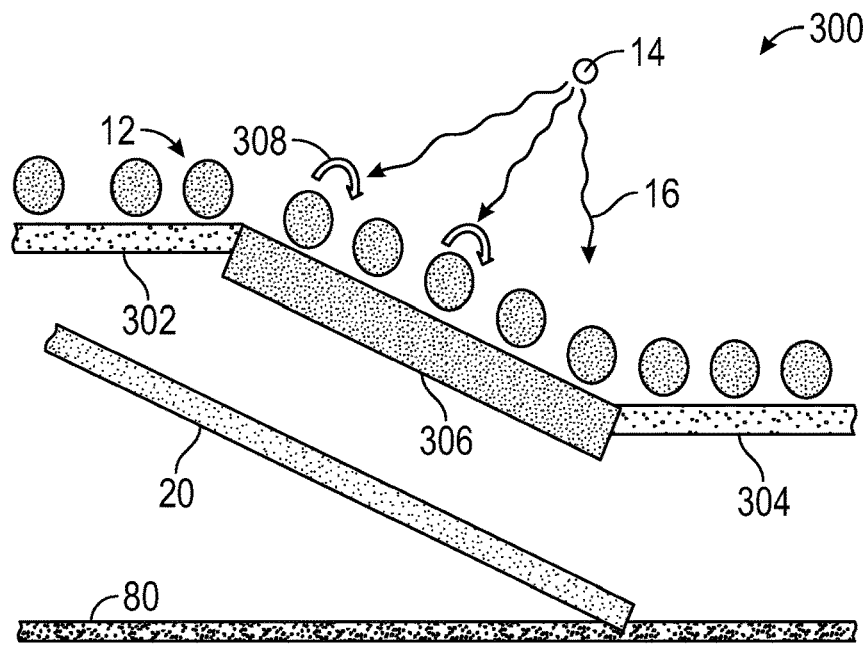
FIG. 9 is a schematic fragmentary diagram illustrating a gravity-assisted loading mechanism useable in the imaging system.

FIG. 9 is a schematic fragmentary diagram illustrating a gravity-assisted loading mechanism 300 that may be used for moving the multiple objects 12. Referring to FIG. 9, an incoming group of the multiple objects 12 is loaded through an incoming ramp 302 and an outgoing group of the multiple objects 12 is unloaded through an outgoing ramp 304. Between the incoming ramp 302 and the outgoing ramp 304 is a transmissive platform 306. The multiple objects 12 are irradiated by the x-ray source 14 as the objects roll down the transmissive platform 306, with respective images being acquired by the detection mechanism 20. The transmissive platform 306 is tilted such that the forward motion of the multiple objects 12 is aided by gravity. As indicated by arrows 308, the multiple objects 12 may be rotated while the images are being acquired. The gravity-assisted loading mechanism 300 may be housed in a protective cabin 80, which may be sealed and maintained at a predetermined temperature and pressure. In some embodiments, the transmissive platform 306 may include an embedded anti-scatter grid. An anti-scatter grid is a device for limiting the amount of scattered radiation reaching the detector, thereby improving the quality of x-ray images.

Referring to FIG. 7, the method 100 proceeds from block 104 to block 106, where the multiple objects 12 are irradiated by the x-ray source 14 (e.g., along the trajectory 204 shown in FIG. 1) and respective images acquired based on the signal intensity detected by the detection mechanism 20. The multiple objects 12 can be scanned in a batch flow manner, where the multiple objects 12 are imaged sequentially as the objects travel along the trajectory 204 between the respective controlled inspection positions 28. Thus, multiple views of each of the objects are acquired. Alternatively, the multiple objects can be scanned in a continuous flow manner, where the multiple objects 12 are continually being imaged as the objects travel (e.g., each detector 24 scans each of the multiple objects 12 travelling continuously along the trajectory 204 in FIG. 1).

In some embodiments, the multiple objects 12 can rotate and change a respective radial angle relative to the x-ray source 14. Each of the respective images may be acquired at a different rotational orientation. The multiple objects 12 may be tilted, canted or pitched to enhance three-dimensional imaging of certain surfaces. The multiple objects 12 can be embedded with respective identifying markers 216 (e.g., represented by the letter R in FIG. 8) that are visible in the respective images. The respective identifying markers 216 are associated with a precise mechanical position at a time the respective images were taken, allowing identification of the multiple objects 12 under inspection.

Per block 108 of FIG. 7, the method 100 includes guiding the multiple objects 12 out of the respective controlled inspection positions 28C. Block 108 can include reconstructing the respective images obtained into a composite image using reconstruction algorithms available to those skilled in the art. As previously noted, the imaging of the multiple objects 12 can be done in two-dimensions or three-dimensions (e.g., cone beam computed tomography and helical computed tomography). The reconstruction may include a filtered back projection algorithm or an iterative algorithm for generating a two-dimensional or three-dimensional image. A filtered back projection is an analytic reconstruction algorithm designed to overcome the limitations of conventional back projection. The filtered back projection applies a convolution filter to remove blurring. An iterative reconstruction algorithm is a technique that uses the differences between the measured data and the calculated data to update an image.

Referring to FIG. 2, when the x-ray source 14 is positioned in an off-center location 15B, it is possible to generate three-dimensional inspection information of the multiple objects 12, without having to rotate the multiple objects 12 while the objects travel through the inspection region 22.

Figure 10:
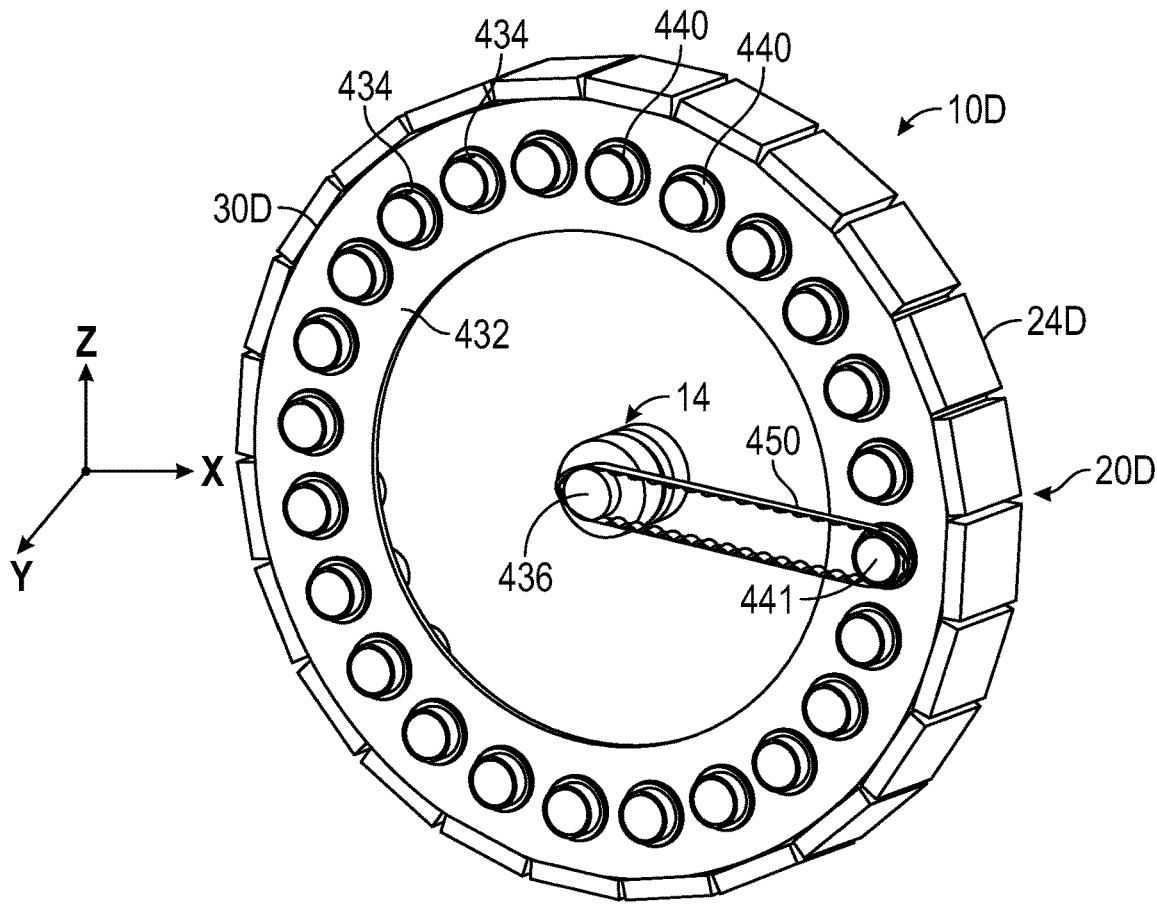
FIG. 10 is a schematic front perspective view of the imaging system in accordance with yet another embodiment of the present disclosure.
Figure 11:
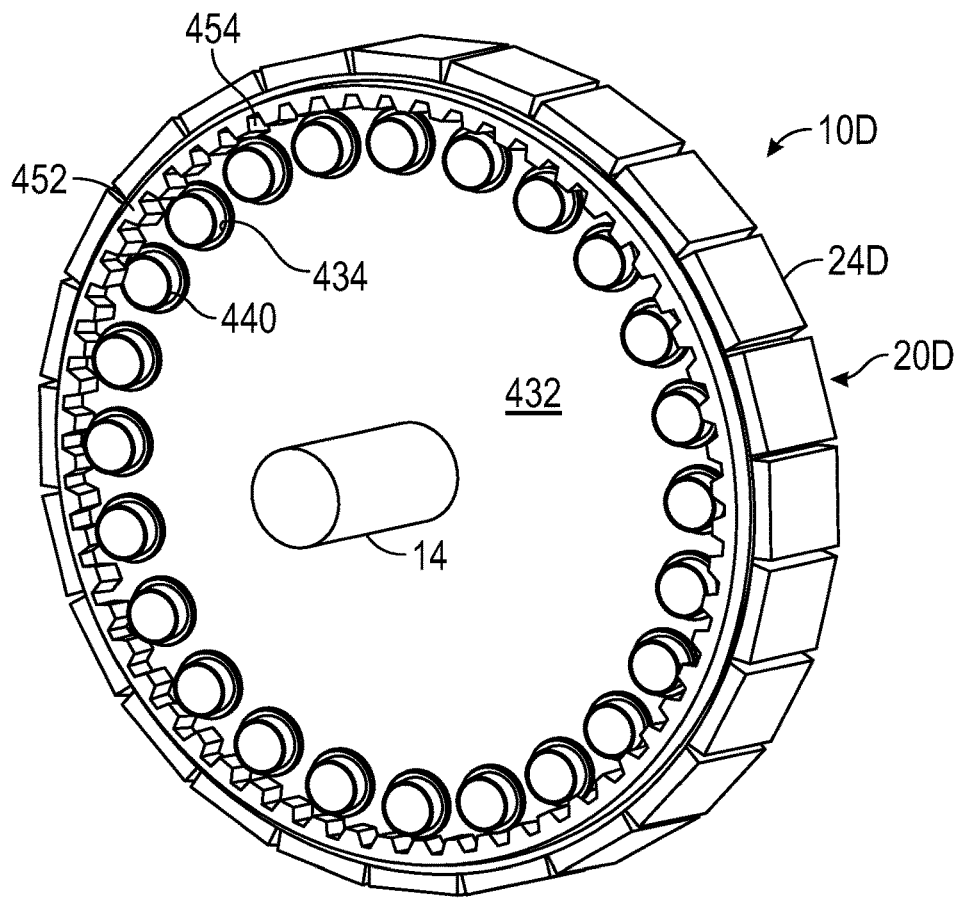
FIG. 11 is a schematic rear perspective view of the imaging system of FIG. 10.
Figure 12:
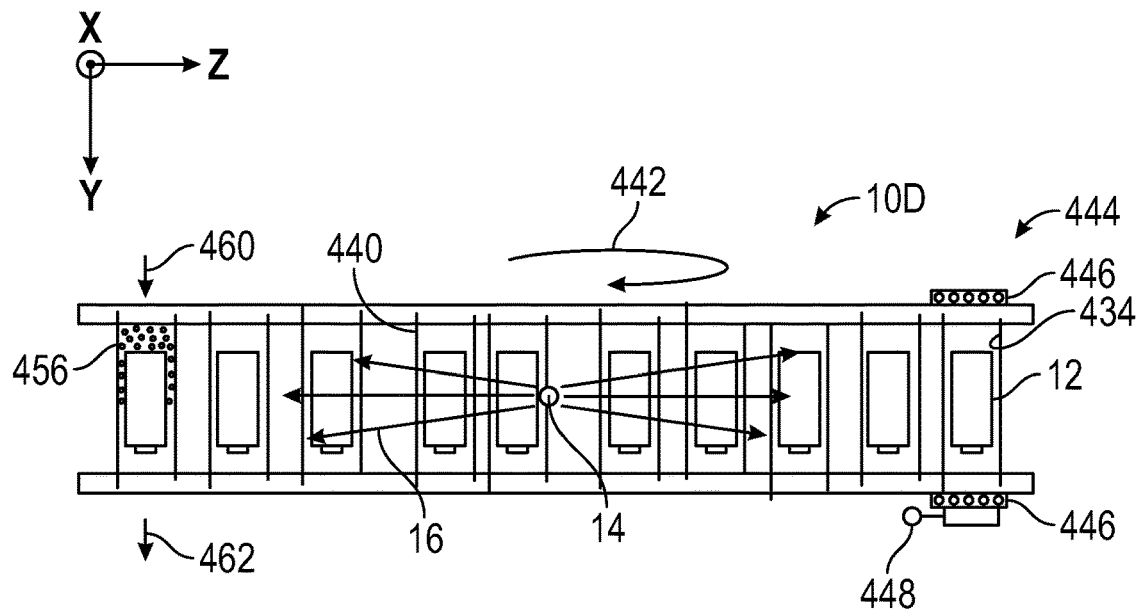
FIG. 12 is a schematic fragmentary side view of the imaging system of FIG. 10.

Referring now to FIGS. 10-12, an imaging system 10D in accordance with yet another embodiment of the present disclosure is shown. FIGS. 10-11 show a front and rear perspective view, respectively, of the imaging system 10D (XYZ axes shown in FIG. 10). Referring to FIGS. 10-11, the imaging system 10D includes a detection mechanism 20D having one or more detectors 24D and an x-ray source 14. FIG. 12 shows a side view of the imaging system 10D along the Y-Z axes, with the detection mechanism 20D omitted for clarity.

Referring to FIG. 12, the imaging system 10D is used to inspect multiple objects 12 that move relative to the x-ray source 14. The multiple objects 12 are moved through a positioning mechanism 30D (see FIG. 10) which includes a wheel body 432 that is rotatable. The wheel body 432 has a plurality of slots 434 that are circumferentially distributed and integral with the wheel body 432. Referring to FIG. 10, the x-ray source 14 can be located within a stationary hub 436 in the center of the wheel body 432. The detection mechanism 20D can be rigidly affixed to an outer surface or perimeter of the wheel body 432, with the one or more detectors 24D at least partially encapsulating the x-ray source 14. Referring to FIGS. 10-12, a plurality of tubes 440 is respectively inserted into the plurality of slots. One or more of the multiple objects 12 (see FIG. 12) is positioned inside each of the plurality of tubes 440. In other words, a single tube of the plurality of tubes 440 can be used to carry several of the objects.

Referring to FIG. 10, the wheel body 432 is rotated along a direction 442, with the multiple objects 12 orbiting the x-ray source 14 as the wheel body 432 is rotated. In some embodiments, the multiple objects 12 travel around the circumference once, thereby completing about 360 degrees of rotation with respect to the stationary hub 436.

Referring to FIG. 12, the imaging system 10D includes a rotation mechanism 444 to selectively rotate the multiple objects 12 around their respective object axes. In the embodiment shown in FIG. 12, the rotation mechanism 444 includes bearings 446 to attach the plurality of tubes 440 to the plurality of slots 434 and allow the plurality of tubes 440 to rotate freely relative to the wheel body 432. Weights 448 can be attached (along the direction of gravity) to align the bearings 446. Other types of rotational devices available to those skilled in the art may be employed.

The plurality of tubes 440 may be driven from two belts. Referring to FIG. 10, a first belt 450 is adapted to be driven from the stationary hub 436 in the center of the wheel body 432, with the first belt 450 being operatively connected to at least one of the plurality of tubes (e.g., tube 441). Referring to FIG. 11, a second belt 452 is adapted to lock the plurality of tubes 440 into a single drive pattern, with the second belt 452 being operatively connected to each of the plurality of tubes 440. The second belt 452 may be attached to an outer periphery of the wheel body 432 and can include grooves 454 that engage with each of the plurality of tubes 440.

Referring to FIG. 10, the imaging system 10D can include a fixation mechanism 456 adapted to prevent the multiple objects 12 from moving within the plurality of tubes 440. In one example, the fixation mechanism 456 is an inflatable device used to apply pressure inside the respective tube, in order to minimize motion of the object inside the tube during inspection. In other embodiments, a vacuum may be applied to minimize motion of the object.

The multiple objects 12 can be loaded (see loading direction 460 in FIG. 10) or inserted into the plurality of tubes 440 in a continuous or stepped fashion. After being scanned by the detection mechanism 20D, the multiple objects 12 are unloaded, (see unloading direction 462 in FIG. 10). The next set of multiple objects 12 to be inspected can then be loaded and the process repeated. Various types of loading and unloading mechanisms may be employed to load and unload the multiple objects 12. The plurality of tubes 440 can be marked with respective x-ray markers in order to determine the orientation of the multiple objects 12 at the time the respective images are taken. Since it can hold many objects at once, the imaging systems described herein can act as a type of magazine, or buffer, for a production line.

The positioning mechanism 30A, 30B and/or detection mechanism 20 may be configured to communicate with the controller 200 (see FIGS. 1 and 7) via cables or wirelessly through a wireless communication device. The various components may be in communication with the controller 200 (and each other) via a wireless network (not shown), which may be a short-range network or a long-range network. The wireless network may be a communication BUS, which may be in the form of a serial Controller Area Network (CAN-BUS). The wireless network may incorporate a Bluetooth connection, a Wireless Local Area Network (LAN) which links multiple devices using a wireless distribution method, a Wireless Metropolitan Area Network (MAN) which connects several wireless LANs or a Wireless Wide Area Network (WAN). Other types of connections may be employed. Accordingly, control of the method 100 may be achieved remotely and the data generated may be transmitted to multiple destinations as desired.

The following Clauses provide representative configurations of imaging systems and methods for imaging as disclosed herein.

Clause 1: An imaging system, comprising: an x-ray source having a beam width greater than or equal to a threshold beam size, wherein multiple objects are irradiated by the x-ray source in respective controlled inspection positions; a detection mechanism adapted to acquire respective images of the multiple objects in the respective controlled inspection positions, the detection mechanism including one or more detectors arranged circumferentially around a central axis; and at least one positioning mechanism adapted to move the multiple objects into and out of the respective controlled inspection positions.

Clause 2: The imaging system of clause 1, wherein the threshold beam size is a width of 110 degrees or an area of 0.9 steradian.

Clause 3: The imaging system of any of clauses 1-2, wherein the detection mechanism includes a plurality of detectors and each of the multiple objects moves between at least two detectors.

Clause 4: The imaging system of any one of clauses 1-3, wherein the multiple objects are adapted to rotate and change a respective radial angle relative to the x-ray source, the respective controlled inspection positions including a plurality of rotational positions of the multiple objects.

Clause 5: The imaging system of any one of clauses 1-4, wherein the x-ray source is positioned along the central axis and the detection mechanism at least partially forms an ellipse around the x-ray source.

Clause 6: The imaging system of any one of clauses 1-4, wherein the x-ray source is positioned in an off-center location relative to the detection mechanism.

Clause 7: The imaging system of any one of clauses 1-6, wherein the detection mechanism includes a line-scan image detector or a direct conversion image detector or a flat panel detector or an indirect conversion image detector with a scintillator.

Clause 8: The imaging system of any one of clauses 1-7, wherein each of the multiple objects defines a respective object axis, and further comprising: at least one rotation mechanism adapted to selectively rotate the multiple objects around the respective object axis, the respective controlled inspection positions including a plurality of rotational positions of the multiple objects.

Clause 9: The imaging system of any one of clauses 1-8, wherein the at least one positioning member is a conveyor belt configured to move the multiple objects in an approximately elliptical fashion around the x-ray source.

Clause 10: The imaging system of any one of clauses 1-9, wherein the multiple objects enter into the respective controlled inspection positions in a direction parallel to the central axis; and the multiple objects leave the respective inspection positions in the direction parallel to the central axis.

Clause 11: The imaging system of any one of clauses 1-10, each of the multiple objects has a fixed relative position to neighboring objects between or in the respective controlled inspection positions.

Clause 12: The imaging system any one of clauses 1-11, the multiple objects enter into the respective controlled inspection positions using a gravity-assisted mechanism, the respective controlled inspection positions including a plurality of rotational positions of the multiple objects.

Clause 13: The imaging system of any one of clauses 1-12, further comprising: a slip-on collimator adapted to at least partially encapsulate an exit window of the x-ray source, the slip-on collimator having an annular body surrounded by a plurality of apertures in order to form multiple effective focal spots.

Clause 14: The imaging system any one of clauses 1-12, wherein further comprising: an integrated collimator positioned around an exit window of the x-ray source, the integrated collimator defining a plurality of apertures integrated with a structure of the x-ray source.

Clause 15: The imaging system of any one of clauses 1-14, further comprising: a controller having a processor and tangible, non-transitory memory on which instructions are recorded; wherein execution of the instructions by the processor causes the controller to selectively guide the multiple objects to the respective controlled inspection positions, via the at least one positioning mechanism, each of the respective controlled inspection positions has a different rotational orientation to the x-ray source; and wherein the controller is configured to acquire an image of at least one of the multiple objects at each of the respective controlled inspection positions and combine multiple images from each of the respective controlled inspection positions into a composite image.

Clause 16: The imaging system of clause 15, wherein the controller is configured to selectively revolve both the detection mechanism and the multiple objects around the central axis at a specified speed.

Clause 17: The imaging system of any one of clauses 1-16, the multiple objects include respective identifying markers that are visible in the respective images, the respective identifying markers being associated with a respective object position at a time the respective images were taken.

Clause 18: The imaging system of any one of clauses 1-17, the at least one positioning member includes a wheel body having a plurality of slots, the x-ray source being located in a center of the wheel body; the wheel body is rotatable and the plurality of slots are circumferentially distributed on a periphery of the wheel body; and the detection mechanism is rigidly affixed to an outer surface of the wheel body, the detection mechanism at least partially forming an ellipse around the x-ray source.

Clause 19: The imaging system of clause 18, further comprising: a plurality of tubes inserted into the plurality of slots, the multiple objects being respectively positioned at least partially within the plurality of tubes; and wherein the plurality of tubes is adapted to rotate freely relative to the wheel body.

Clause 20: The imaging system of clause 19, further comprising: a first belt adapted to be driven from a fixed hub in the center of the wheel body, the first belt being operatively connected to at least one of the plurality of tubes.

Clause 21: The imaging system of clause 20, further comprising: a second belt adapted to lock the plurality of tubes into a single drive pattern, the second belt being operatively connected to each of the plurality of tubes.

Clause 22: The imaging system of any one of clauses 19-21, further comprising: at least one fixation mechanism positioned in the plurality of tubes, the at least one fixation mechanism being adapted to prevent the multiple objects from respectively moving within the plurality of tubes.

Clause 23: The imaging system of any one of clauses 19-22, wherein a first set of the multiple objects are adapted to be loaded into the plurality of tubes continuously or in parallel, the wheel body being rotated such that the first set travels around the periphery of the wheel body; and the first set of the multiple objects are unloaded from the plurality of tubes continuously or in parallel after being scanned by the detection mechanism.

Clause 24: A method, comprising: providing an x-ray source having a beam width greater than or equal to a threshold beam size, wherein multiple objects are irradiated by the x-ray source in respective controlled inspection positions; moving the multiple objects into and out of the respective controlled inspection positions, via at least one positioning member; and acquiring respective images of the multiple objects in the respective controlled inspection positions, via a detection mechanism in an imaging system, the detection mechanism including one or more detectors arranged circumferentially around a central axis.

Clause 25: The method of clause 24, wherein the imaging system has a controller with a processor and tangible, non-transitory memory, the method further comprising: guiding the multiple objects in the respective controlled inspection positions along the detection mechanism, via the controller; acquiring respective images of the multiple objects, each of the respective images being acquired at a different rotational orientation, via the detection mechanism; and combining the respective images into a respective composite image of the multiple objects, via the controller.

Clause 26: The method of either of clauses 24 or 25, further comprising: scanning the multiple objects in a batch flow manner such that the multiple objects are imaged sequentially in a trajectory between the respective controlled inspection positions.

Clause 27: The method of either of clauses 24 or 25, further comprising: scanning the multiple objects in a continuous flow manner such that the multiple objects are imaged continually in a trajectory between the respective controlled inspection positions.

Clause 28: A imaging system, comprising: x-ray source means for generating a beam with a beam width greater than or equal to a threshold beam size wherein multiple objects are irradiated in respective controlled inspection positions by the x-ray source means; detector means for acquiring respective images of the multiple objects in the respective controlled inspection positions, the detector means including one or more detectors arranged circumferentially around a central axis; and positioning means for moving the multiple objects into and out of the respective controlled inspection positions.

Clause 29: The imaging system of clause 28, further comprising: scanning means for scanning the multiple objects in a batch flow manner such that the multiple objects are imaged sequentially in a trajectory between the respective controlled inspection positions.

The controller 200 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, a physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file rechargeable energy storage system, an application database in a proprietary format, a relational database energy management system (RDBMS), etc. Each such data store may be included within a computing device employing a computer operating system such as one of those mentioned above and may be accessed via a network in one or more of a variety of manners. A file system may be accessible from a computer operating rechargeable energy storage system and may include files stored in various formats. An RDBMS may employ the Structured Query Language (SQL) in addition to a language for creating, storing, editing, and executing stored procedures, such as the PL/SQL language mentioned above.

The flowcharts in the drawings illustrate an architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by specific purpose hardware-based rechargeable energy storage systems that perform the specified functions or acts, or combinations of specific purpose hardware and computer instructions. These computer program instructions may also be stored in a computer-readable medium that can direct a controller or other programmable data processing apparatus to function in a particular manner, such that the instructions stored in the computer-readable medium produce an article of manufacture including instructions to implement the function/act specified in the flowchart and/or block diagram blocks.

The numerical values of parameters (e.g., of quantities or conditions) in this specification, including the appended claims, are to be understood as being modified in each respective instance by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of each value and further divided ranges within the entire range. Each value within a range and the endpoints of a range are hereby disclosed as separate embodiments.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112 ¶116. Embodiments of the disclosure in which an exclusive property or privilege is claimed are defined as follows.

What is claimed is:

1. An imaging system, comprising:
   an x-ray source having a beam width greater than or equal to a threshold beam size, wherein multiple objects are irradiated by the x-ray source in respective controlled inspection positions, the x-ray source comprising an exit window encircling an anode;
   a detection mechanism adapted to acquire respective images of the multiple objects in the respective controlled inspection positions, the detection mechanism including one or more detectors arranged circumferentially around a central axis; and
   a positioning mechanism adapted to move the multiple objects into and out of the respective controlled inspection positions, wherein:
   the detection mechanism includes a first detector and a second detector;
   a first detection surface of the first detector faces the central axis;
   a second detection surface of the second detector faces the central axis such that a first line perpendicular to the first detection surface is angled relative to a second line perpendicular to the second detection surface; and
   the x-ray source is configured to irradiate the multiple objects in the respective controlled inspection positions at the same time such that multiple detectors of the detection mechanism acquire the respective images of the multiple objects at the same time.

2. The imaging system of claim 1, wherein the threshold beam size is a width of 110 degrees or an area of 0.9 steradian.

3. The imaging system of claim 1, wherein the detection mechanism includes a plurality of detectors and each of the multiple objects moves between at least two detectors.

4. The imaging system of claim 1, wherein:
   the multiple objects are adapted to rotate and change a respective radial angle relative to the x-ray source, the respective controlled inspection positions including a plurality of rotational positions of the multiple objects.

5. The imaging system of claim 1, wherein the x-ray source is positioned along the central axis and the detection mechanism at least partially forms an ellipse around the x-ray source.

6. The imaging system of claim 1, wherein the x-ray source is positioned in an off-center location relative to the detection mechanism.

7. The imaging system of claim 1, wherein the detection mechanism includes a line-scan image detector or a direct conversion image detector or a flat panel detector or an indirect conversion image detector with a scintillator.

8. The imaging system of claim 1, wherein each of the multiple objects defines a respective object axis, and further comprising:
   at least one rotation mechanism adapted to selectively rotate the multiple objects around the respective object axis, the respective controlled inspection positions including a plurality of rotational positions of the multiple objects.

9. The imaging system of claim 1, wherein:
   the positioning mechanism is a conveyor belt configured to move the multiple objects in an approximately elliptical fashion around the x-ray source.

10. The imaging system of claim 1, wherein:
    the multiple objects enter into the respective controlled inspection positions in a direction parallel to the central axis; and
    the multiple objects leave the respective inspection positions in the direction parallel to the central axis.

11. The imaging system of claim 1, wherein:
    each of the multiple objects has a fixed relative position to neighboring objects between or in the respective controlled inspection positions.

12. The imaging system of claim 1, wherein:
    the multiple objects enter into the respective controlled inspection positions using a gravity-assisted mechanism, the respective controlled inspection positions including a plurality of rotational positions of the multiple objects.

13. The imaging system of claim 1, further comprising:
    a slip-on collimator adapted to at least partially encapsulate the exit window of the x-ray source, the slip-on collimator having an annular body surrounded by a plurality of apertures in order to form multiple effective focal spots.

14. The imaging system of claim 1, further comprising:
    an integrated collimator positioned around the exit window of the x-ray source, the integrated collimator defining a plurality of apertures integrated with a structure of the x-ray source.

15. The imaging system of claim 1, further comprising:
    a controller having a processor and tangible, non-transitory memory on which instructions are recorded;
    wherein execution of the instructions by the processor causes the controller to selectively guide the multiple objects to the respective controlled inspection positions, via the positioning mechanism, each of the respective controlled inspection positions has a different rotational orientation to the x-ray source; and
    wherein the controller is configured to acquire an image of at least one of the multiple objects at each of the respective controlled inspection positions and combine multiple images from each of the respective controlled inspection positions into a composite image.

16. The imaging system of claim 15, wherein the controller is configured to selectively revolve both the detection mechanism and the multiple objects around the central axis at a specified speed.

17. The imaging system of claim 1, wherein:
the multiple objects include respective identifying markers that are visible in the respective images, the respective identifying markers being associated with a respective object position at a time the respective images were taken.

18. The imaging system of claim 1, wherein:
the positioning mechanism includes a wheel body having a plurality of slots, the x-ray source being located in a center of the wheel body;
the wheel body is rotatable and the plurality of slots are circumferentially distributed on a periphery of the wheel body; and
the detection mechanism is rigidly affixed to an outer surface of the wheel body, the detection mechanism at least partially forming an ellipse around the x-ray source.

19. The imaging system of claim 18, further comprising:
a plurality of tubes inserted into the plurality of slots, the multiple objects being respectively positioned at least partially within the plurality of tubes; and
wherein the plurality of tubes is adapted to rotate freely relative to the wheel body.

20. The imaging system of claim 19, further comprising:
a first belt adapted to be driven from a fixed hub in the center of the wheel body, the first belt being operatively connected to a tube of the plurality of tubes.

21. The imaging system of claim 19, further comprising:
a second belt adapted to lock the plurality of tubes into a single drive pattern, the second belt being operatively connected to each of the plurality of tubes.

22. The imaging system of claim 19, further comprising:
at least one fixation mechanism positioned in the plurality of tubes, the at least one fixation mechanism being adapted to prevent the multiple objects from respectively moving within the plurality of tubes.

23. The imaging system of claim 19, wherein:
a first set of the multiple objects are adapted to be loaded into the plurality of tubes continuously or in parallel, the wheel body being rotated such that the first set travels around the periphery of the wheel body; and
the first set of the multiple objects are unloaded from the plurality of tubes continuously or in parallel after being scanned by the detection mechanism.

24. A method, comprising:
providing an x-ray source having a beam width greater than or equal to a threshold beam size, wherein multiple objects are irradiated by the x-ray source in respective controlled inspection positions, the controlled inspection positions encircling the x-ray source in a plane that passes through the x-ray source;
moving the multiple objects into and out of the respective controlled inspection positions, via a positioning member; and
acquiring respective images of the multiple objects in the respective controlled inspection positions, via a detection mechanism in an imaging system, the detection mechanism including one or more detectors arranged circumferentially around a central axis, wherein:
multiple detectors are irradiated by the x-ray source simultaneously such that a plurality of the multiple objects is imaged simultaneously by the multiple detectors, each detector comprising a detection surface oriented towards the x-ray source with a line perpendicular to the detection surface angled relative to another detector.

25. The method of claim 24, wherein the imaging system has a controller with a processor and tangible, non-transitory memory, the method further comprising:
guiding the multiple objects in the respective controlled inspection positions along the detection mechanism, via the controller;
acquiring respective images of the multiple objects, each of the respective images being acquired at a different rotational orientation, via the detection mechanism; and
combining the respective images into a respective composite image of the multiple objects, via the controller.

26. An imaging system, comprising:
an x-ray source for generating a beam with a beam width greater than or equal to a threshold beam size, wherein the x-ray source is configured to irradiate multiple objects simultaneously in respective controlled inspection positions, the respective controlled inspection positions being arranged circumferentially around a central axis, encircling the x-ray source, and being arranged in a plane that passes through the x-ray source perpendicular to the central axis;
a detector mechanism for acquiring respective images of the multiple objects in the respective controlled inspection positions, the detector mechanism including one or more detectors arranged circumferentially around the central axis, the one or more detectors encircling the x-ray source and being arranged in the plane that passes through the x-ray source perpendicular to the central axis; and
a positioning mechanism for moving the multiple objects into and out of the respective controlled inspection positions.

27. The system of claim 26, further comprising:
a scanner for scanning the multiple objects in a batch flow manner such that the multiple objects are imaged sequentially in a trajectory between the respective controlled inspection positions.

* * * * *